United States Patent [19]

Hartnett et al.

[11] Patent Number: 5,106,613
[45] Date of Patent: * Apr. 21, 1992

[54] HAIR CONDITIONING SHAMPOO

[75] Inventors: Donna A. Hartnett, Dayton; Charles Reich, Highland Park; Amrit M. Patel, Dayton; Clarence R. Robbins, Martinsville, all of N.J.

[73] Assignee: Colgate-Palmolive Company, Piscataway, N.J.

[*] Notice: The portion of the term of this patent subsequent to Mar. 5, 2008 has been disclaimed.

[21] Appl. No.: 640,663

[22] Filed: Jan. 14, 1991

Related U.S. Application Data

[63] Continuation of Ser. No. 507,328, Apr. 9, 1990, Pat. No. 4,997,641.

[51] Int. Cl.$^5$ .......................... A61K 7/06; A61K 7/09; A61K 7/11
[52] U.S. Cl. ........................................ 424/71; 424/70; 424/DIG. 4; 514/880; 514/881; 252/89.1; 252/153; 252/173; 252/174.15; 252/174.21; 252/544; 252/547; 252/550; 252/551
[58] Field of Search .................... 424/70, 71, DIG. 4; 514/880, 881

[56] References Cited

U.S. PATENT DOCUMENTS

| | | | |
|---|---|---|---|
| 4,330,526 | 5/1982 | Watanabe et al. | 424/70 |
| 4,786,494 | 11/1988 | Hirota et al. | 424/70 |
| 4,795,632 | 1/1989 | Giede et al. | 424/70 |
| 4,938,953 | 7/1990 | Pena et al. | 424/70 |
| 4,992,266 | 2/1991 | Knoll | 424/70 |
| 4,997,641 | 3/1991 | Hartnett et al. | 424/70 |

*Primary Examiner*—Thurman K. Page
*Assistant Examiner*—Donald R. McPhail
*Attorney, Agent, or Firm*—Richard J. Ancel; Robert C. Sullivan

[57] ABSTRACT

A hair conditioning shampoo is described, which contains $C_6$, $C_8$ and/or $C_{10}$ alkyl sulfate and/or $C_6$, $C_8$ and/or $C_{10}$ alkyl lower alkoxylate sulfate as an anionic detergent component, a water insoluble conditioning agent(s) from the group of silicones (preferably a certain type of aminosilicone), polyethylenes, paraffins, isoparaffins, microcrystalline waxes, $C_{18\text{-}36(mixed)}$ fatty acids or such triglycerides, high fatty alcohol ester of a high fatty acid (such as stearyl stearate), beeswax, cationic conditioning agent, such as a quaternary ammonium or any mixture thereof, and a stabilizer for the shampoo, in water. Among adjuvants that may be present are lauric monoethanolamide, cocodiethanolamide, and hydroxyethyl cellulose, other thickeners and viscosity modifiers, pH adjusting agents, antioxidants perfumes and colorants. The presence of the $C_6$, $C_8$ and/or $C_{10}$ alkyl sulfate and/or $C_6$, $C_8$ and/or $C_{10}$ alkyl lower alkoxylated sulfate surprisingly improves conditioning of the hair, compared to shampoos containing other detergents that contain longer chain alkyl groups.

9 Claims, No Drawings

HAIR CONDITIONING SHAMPOO

This is a continuation of application Ser. No. 07/507,328, filed 4/9/90, now U.S. Pat. No. 4,997,642.

This invention relates to hair conditioning compositions. More particularly, it relates to shampoos for washing and conditioning human hair, which improve its combability and manageability, compared to ordinary shampoos or shampoos made with "conventional" anionic detergnets.

Hair conditioning shampoos are well known in the cosmetic art and are described in many patents and patent applications. Cationic surfactants, such as quaternary ammonium salts, have been employed in hair rinses and in shampoos as conditioning agents, as have been various water insoluble conditioning agents, such as silicones, waxes greases and oils. Shampoos have been made in different forms, including solid, gel, creme, and liquid forms, and such liquids have been produced as solutions, emulsions, and suspensions or dispersions.

In an application for patent entitled Hair Conditioning Shampoo Containing Long Chain Alcohol Component, identified by attorney's docket No. IR 4741A-4801/4 CIP, which is being filed on the same day as the present application, there were described shampoos containing lipophile sulfate(s) and a long chain saturated alcohol or "derivative" thereof, as a stabilizing agent, pearlescent agent and conditioning improver. The present invention further improves the conditioning by such and similar shampoos, which improvement was unobvious and unpredictable.

In accordance with the present invention a hair conditioning shampoo of improved hair conditioning properties due to its content of $C_6$, $C_8$ and/or $C_{10}$ alkyl sulfate and/or $C_6$ $C_8$ and/or $C_{10}$ alkyl lower alkoxy sulfate instead of other anionic detergent, comprises an anionic detergent which is a $C_6$, $C_8$ and/or $C_{10}$ alkyl sulfate and/or a $C_6$, $C_8$ and/or $C_{10}$ alkyl lower alkoxy sulfate, a water insoluble hair conditioning agent, a stabilizer and an aqueous medium, which may include adjuvants and other components of such shampoos.

A search of the prior art has resulted in the finding of the following U.S. Pat. Nos.:

| | | |
|---|---|---|
| 3,969,500; | 4,707,293; | 4,824,602; |
| 4,024,078; | 4,726,944; | 4,850,732; |
| 4,470,982; | 4,728,457; | 4,885,130; and |
| 4,701,322; | 4,731,201; | 4,859,500 |
| 4,704,272; | 4,803,237; | |

Also of interest is the Petrolite Corporation brochure entitled Unilin TM Alcohols, copyrighted in 1985 and identified as SP-1040.

Although the art found describes conditioning agents in shampoos and the uses of lower alkyl ethoxy sulfates to remove quaternary ammonium salts and complexes from hair (U.S. Pat. No. 4,731,201) and of decyl in liquid detergents to improve cleaning, U.S. Pat. No. 4,024,078) there is no teaching in any of the references nor in any combination thereof that would lead one to the present invention or that would lead one to expect to obtain the advantages thereof.

In a broader aspect of this invention the shampoo may be in liquid, creme, gel or paste form and needs only to comprise the $C_{6-10}$ (equivalent to $C_6$, $C_8$ and/or $C_{10}$) lipophile sulfate detergent, the water insoluble hair conditioning agent(s) and the stabilizer in an aqueous medium. In some such forms stabilization, effectable by the presence of a long chain saturated primary alcohol or other suitable stabilizer, may be unnecessary, but its presence may be desirable to obtain other advantages of such compounds, including pearlescing effect and improvement in conditioning.

When cationic surface active conditioning agents are employed they may be considered to be secondary conditioning agents in the invented conditioning compositions. They are preferably quaternary ammonium salts, although other surface active cationic compounds of fiber conditioning properties may also be employed, at least in part. Thus, known amines, amine salts, imidazolinium salts and betaines, and such cationic materials as are described in U.S. Pat. No. 4,000,077 may be substituted for at least some of the quaternary ammonium salt, as may be complexes of cationic and anionic surfactants, such as have been described in U.S. Pat. Nos. 4,786,422 and 4,888,119 and in U.S. patent application Ser. No. 06,916,069.

The preferred quaternary ammonium salts are of the formula:

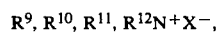

which may also be shown as

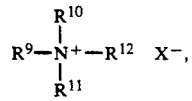

wherein at least one of the R groups is lower alkyl and at least one is higher alkyl, with the others being higher and/or lower alkyl. Preferably $R^9$ is lower alkyl, such as of 1 to 4 carbon atoms, $R^{10}$ and $R^{11}$ are higher alkyls of 10 to 40 carbon atoms, $R^{12}$ is such a higher alkyl or lower alkyl, and $X^-$ is a salt-forming anion, such as halide, lower alkosulfate or lower carboxylic acid radical, e.g., chloride, bromide, methosulfate, ethosulfate, citrate or acetate. The lower alkyl will preferably be of 1 to 3 carbon atoms, more preferably being of 1 or 2 carbon atoms, and most preferably, in most cases, will be methyl, and the higher alkyl will preferably be of 10 to 22 carbon atoms, more preferably 12 to 18 or 20 carbon atoms, and most preferably of 14 to 18 carbon atoms, e.g., 16 or 18 carbon atoms. The anion is preferably a halogen, such as chlorine, bromine, or iodine, with chlorine and bromine being preferred and with chlorine being more preferred.

The number of lower alkyls on the quaternary nitrogen will preferably be 1 or 2 and the number of higher alkyls will usually be 2 or 3. It has been found to be desirable to have at least 30 carbon atoms in the quaternary ammonium salt and preferably at least 34. The most preferred higher alkyls are cetyl and stearyl and the most preferred lower alkyl is methyl. The more preferred quaternary ammonium halides include tricetyl methyl ammonium chloride and distearyl dimethyl ammonium chloride, but other such quaternary ammonium salts, are also operative, including dicetyl dimethyl ammonium chloride and tristearyl methyl ammonium chloride, corresponding bromides, amines, amine salts, betaines and complexes of the previously mentioned U.S. patents, which are hereby incorporated by reference. Such alternative cationic surfactants and complexes may be employed as at least part of the cationic surfactant content of the invented compositions. However, it is preferred to use a mixed distearyl dimethyl ammonium chloride and tricetyl methyl ammonium chloride, in a ratio in the range of 0.3 to 3.

Among the other (primary) water insoluble hair conditioning agents those which are more preferred include organosilicon compounds, such as the dimethicones and silicones (especially aminosilicones), polyethylenes, paraffins, petrolatums, microcrystalline waxes, $C_{18-36}$ (mixed) fatty acids and mixed triglycerides, and stearyl stearates (and other higher esters). The organosilicon compounds and the silicones that may be employed include any of those which are hair conditioning agents intended for use in conditioning shampoos, various of which have been described in the previously mentioned patents and applications. They are preferably of non-volatile types. It has been found that aminosilicones are usually more effective conditioning agents in the compositions of this invention than are conventional silicones, and of the aminosilicones the present special types described herein are better yet. Thus, it is much preferred to utilize an aminosilicone of the formula

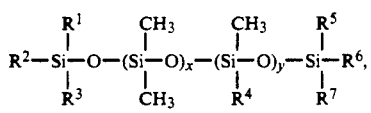

wherein $R^1$, $R^2$, $R^3$, $R^5$, $R^6$ and $R^7$ are alkyls of 1 to 6 carbon atoms, and most preferably of 1 carbon atom each, $R^4$ is $-R^8-NH-CH_2CH_2{-}_{NH_2}$, $R^8$ is alkylene of 3 to 6 carbon atoms, and most preferably is an isobutyl group, x is an average number in the range of 1 to 10, more preferably less than 5, and most preferably 1, which is of an amine equivalent in the range of 4,000 to 60,000. Preferably, x is in the range of 200 or 300 to 10,000, more preferably 500 to 10,000, and most preferably 750 to 800 or 850, e.g., about 800, and y is in the range of 0 to 8, more preferably being less than 3 and most preferably being about 1. The amine equivalent of such aminosilicone is preferably in the range of 5,000 to 50,000, more preferably 10,000 to 40,000. For the specific preferred aminosilicone utilized in the experiment reported in this specification the molar percentage of amine is about 0.125, the degree of polymerization is about 800, x is 797, y is one, and the molecular weight is about 60,000 daltons. Because molecular weights of high polymers sometimes vary, depending on the measurement technique utilized, it is suggested that primary reference should be to the formula for identification of the aminosilicones described, rather than placing primary reliance on the molecular weights given. The described preferred aminosilicone is available from Dow Corning Corporation, and it is identified in the working examples herein as Dow Corning Aminosilicone A (applicants' identification).

The polyalkylenes that may be employed as water insoluble conditioning agents in the present compositions are preferably those of a molecular weight in the range of 1,000 to 5,000, more preferably 1,000 to 4,000 and still more preferably 2,000 to 2,500, e.g., about 2,000. Oxidized versions of these polyalkylene polymers may also be used, which create larger hydrocarbons with terminal carboxyl groups. Although the alkylenes of these polymers will usually be ethylene, it is within the invention to employ polymers of hydrocarbons of 1 to 5 carbon atoms each, preferably 2 to 3 carbon atoms, in which the molecular weight range may be from 1,000 to 10,000, or even more, under some conditions. Usually however, the polymers will be of ethylene and/or propylene, and almost always of ethylene.

Paraffins that may be utilized will normally be of chain lengths of 20 to 50 carbon atoms, preferably 20 to 40 carbon atoms, and isoparaffins can be of chain lengths in the range of 12 to 16 carbon atoms, preferably 13 to 14 carbon atoms. The petrolatums are petroleum jellies or mineral jellies which melt in the range of 38° to 60° C. and the microcrystalline waxes are of an average molecular weight in the range of about 500 to 800 (which is about twice that of the paraffins). $C_{18-36}$ fatty acid triglycerides are higher triglycerides which are available from Croda Chemical Corporation under the tradename Syncrowax (HGL-C, for example). Stearyl stearate, which is representative of useful esters of both higher fatty alcohols and higher fatty acids, is available from Inolex Corporation, as Lexol SS. This and related compounds, such as other higher fatty esters, may also act as stabilizers for the shampoo, preventing settlings out of components and phase separations.

The long chain primary alcohol, which may desirably be included in the compositions of this invention, is preferably a saturated compound, with the hydroxy group being terminally located. Such alcohol will normally be of a distribution of homologous alcohols and typically all are of even numbers of carbon atoms, averaging 24 to 45 carbon atoms (on a weight basis), preferably 28 to 42 carbon atoms, more preferably about 30 to 40 carbon atoms and most preferably 30 to 40 carbon atoms. When the average number of carbon atoms in the chain is less than 24 the desired effectiveness of such alcohols in the present formulations is decreased, with the stabilization, fiber conditioning and pearlescing actions being diminished, and when such chain length is more than 45 carbon atoms, e.g., of an average of about 50 carbon atoms, such alcohols are not satisfactorily dispersible in the described compositions. In addition to the mentioned long chain alcohols, related compounds such as corresponding alkoxylated alcohols, corresponding fatty acids and long chain saturated primary alcohol esters, may be substituted, at least in part. Ethoxylated alcohols are preferred as the alkoxylated alcohols and will normally contain up to 20 ethoxy groups per mole, such as 10 to 20, e.g., about 13 or 15. However, the preferred alcohols normally will be employed alone or in mixture with related compounds from the "derivatives" group, with the alcohol being the major proportion of the final "alcohol plus derivatives" content. Examples of commercial materials which may be employed in the present compositions are those manufactured by Petrolite Corporation and sold through Petrolite Specialty Polymers Group under the name Unilin TM Alcohols, as described in the technical bulletin previously referred to in this specification. Such alcohols may be 75 to 90%, e.g., 80 to 85%, of the commercial product, with the balance being substantially all saturated hydrocarbons of equivalent chain lengths. In such products the distribution curve for the alcohol is substantially bell-shaped, with no chain length of alcohol being more than 10% of the total content thereof, and with the corresponding hydrocarbon content being of a substantially flat distribution curve, with about 1 or 2% of each of the hydrocarbons being present. Such distribution curves, as bar graphs, are given in the Petrolite bulletin previously mentioned. The alcohols (and corresponding hydrocarbons) present will normally be of chain lengths such that at least 80% are in the range of 20 to 54 carbon atoms, at least 80% being in the range of about 18 or 20 to 44 carbon atoms for an alcohol averaging about 30 carbon atoms and at least 80% being in the range of about 28 or 30 to 54 carbon atoms when the alcohol averages about 40 carbon atoms. Examples of the long chain primary alcohols are Unilin-425 alcohol, which averages 30 carbon atoms in its chain, Unilin-550 alcohol, which averages 40 carbon atoms in its chain, and Unilin 350, which averages 26 carbon atoms in its chain. A derivative, Unithox-550, is an ethoxylated such alcohol of an average of 40 carbon atoms in its alkyl chain, ethoxylated with up to 20 ethoxy groups, e.g., 13.

The special water soluble synthetic organic anionic detergent, which is present in the shampoos of this invention, is a lipophile sulfate although lipophile sulfonates of similar types (with only the sulfate being replaced by sulfonate) may sometimes be substituted, at least in part.

The lipophile sulfate of the present invented compositions, which surprisingly improves the conditioning effect thereof, may be either an alkyl sulfate or an alkoxylated alkyl sulfate wherein the alkyl is of $C_{6-10}$ or approximately of (about) 6 to 10 carbons, and the alkoxy is of 1 to 6 carbon atoms, preferably 2 or 3, more preferably being ethoxy, with 1 to 6 ethoxies being present in the alkoxylated compound. Although pure compounds would be desirable they haven't been available at reasonable prices so the alkyl sulfates and the alkoxylated alkyl sulfates are normally mixtures of materials which average $C_{6-10}$ carbon atoms in the fatty alkyl and preferably average 2 or 3 ethoxy groups per mole for the ethoxylated alkyl sulfates. Although broad range ethoxylates (BRE's) are also useful it is preferred to employ narrow range ethoxylates (NRE's) and one reason for that preference is that they tend to produce shampoos of higher viscosities, which are often desirable. The alkyl group distribution for the alkyl sulfates and for the ethoxylated alkyl sulfates will desirably be such that at least 80% of the corresponding alcohols is in the range of 6 to 12 carbon atoms, with the average being in the range of 6 to 10 carbon atoms, but because many of the starting materials employed are natural materials or are synthesized by processes which do not result in narrow range chain length products, broader distributions are also employable. Similarly, the ethoxylates include at least 80% of the ethoxylated alcohol equivalent within one ethoxy group of that designated, for example, 80% of a 3 EtO product will be of 2 to 4 EtO's.

The salt forming cation of such compounds is normally alklai metal, ammonium or alkanolamine, with sodium and ammonium salts being preferred, especially sodium.

Although it is preferred that the anionic detergent(s) employed should include the hexyl, octyl and/or decyl group(s), it is also within the invention to utilize other anionic detergents with those which are preferred. In such other anionic detergents the lipophile group will include a higher fatty alkyl of 12 to 18 or 20 carbon atoms, such as sulfates and lower alkoxy sulfates, e.g., sodium lauryl sulfate, sodium lauryl diethoxy sulfate, and corresponding ammonium and triethanolamine salts. Also useful are the $C_{12-18}$ alkyl paraffin sulfonates, olefin sulfonates, tridecylbenzene sulfonates and $C_{12-16}$ acyl monoglyceride sulfates. Other such anionic detergents are described in *McCutcheon's Detergents and Emulsifiers*, North American Edition, published in 1984. Such detergents often contribute significantly to better cleaning power of the invented shampoos, which are illustrated in the Examples. Additionally, it may be desirable to employ amphoteric, ampholytic and zwitterionic detergents in such compositions and sometimes, relatively small proportions of nonionic detergents, and such are also described in such publication. Also, see the description of suitable detergents in Ser. No. 07/432,952, previously referred to here To make the invented compositions the various required components are dissolved and/or suspended in an aqueous medium. Such medium may include various non-interfering normal shampoo composition constituents known in the art, but a few of these will be specifically mentioned herein because they are especially desirable components of the present compositions and contribute in a significant manner to its desirable properties. Higher fatty alkanolamides have long been known as foaming agents and foam stabilizers. Such compounds will usually be of 12 to 16 carbon atoms in the acyl group, which is reacted with a lower (1 to 3 carbon atoms) mono- or dialkanolamine. In the present formulations the best alkanolamides are considered to be lauric monoethanolamide and cocoethanolamide. However, other known foam stabilizers and foaming agents may also be employed, too, in whole or in part, such as the betaines and related materials. Various gums and other thickening materials are also useful in shampoo compositions but it has been found that the best of these in the present compositions are hydroxy ethyl celluloses. Such are available from Aqualon Corporation under the trademark Natrosol, such as Natrosol 250 HHR and Natrosol 330 CS, which preferably are employed in mixture, with the content of the former being from 2 to 5 times that of the latter. However, other suitable gums and thickeners may also be employed, such as hydroxypropylmethyl cellulose, methyl cellulose, modified starches and guar gum. Another important constituent of the present composition is mineral oil, when polyethylene is employed as a hair conditioning agent. The mineral oil is employed to solubilize and to help disperse the polyethylene, which, if not satisfactorily dispersed in the composition, will be of little hair conditioning effect and tends to settle out.

Other components of the present compositions which may be employed include: ethylene glycol monostearate, ethylene glycol distearate and propylene glycol distearate, all of which have pearlescing properties; viscosity control agents, such as propylene glycol and sodium chloride; pH adjusting agents, such as citric acid and citrates; sequestrants, such as EDTA; antifreezes, such as propylene glycol; solvents, such as ethanol and isopropanol; preservatives and antioxidants, such as Germaben II (Sutton Laboratories); anti-dandruff agents, such as zinc pyrithione and Climbazole TM (see U.S. Pat. No. 4,867,971); colorants an perfume. Water, employed to make the aqueous medium, but which may be present not only in liquid preparations but also in gels, pastes and cremes, is preferably filtered, irradiated and deionized water of essentially zero hardness but it may also be tap water, although it is preferred to keep the hardness below 50 p.p.m., as calcium carbonate. However, other tap waters of hardnesses as high as 200 p.p.m. will sometimes also be useful, but usually they will be avoided.

The proportions of the various components present in the invented liquid conditioning and shampoo compositions to obtain the described desirable properties will now be given. The cationic conditioner, when present, is in a hair conditioning or conditioning supplementing proportion, which will normally be in the range of 0.1 or 0.2 to 10% or 0.1 or 0.2 to 5% of the invented shampoos, preferably being 0.2 to 3% and more preferably being 0.3 to 0.7 or to 2%. The content of water insoluble non-cationic conditioning agent(s) (in addition to the cationic conditioner) will be a hair conditioning proportion or such a proportion which, alone or in conjunction with the cationic conditioner present, serves satisfactorily to condition the hair simultaneously with shampooing, which will normally be in the range of 0.1 or 0.2 to 10%, preferably 0.3 to 7%, and more preferably 0.5 to 5%. The long chain saturated primary alcohol and/or "derivatives" thereof, when present, will normally total 0.5 to 10%, preferably 0.5 to 4%, and more preferably 1 to 3.5%. If another stabilizer is employed instead, such as a higher ester, the same ranges can apply. The content of aqueous medium (which may include various adjuvants) will normally be in the range of 75 to 98%, with the water content of such a shampoo being 60 to 90%, preferably 65 to 85%, and more preferably 65 to 80%. However, the water and aqueous medium contents may be varied, depending on the proportions of adjuvants desirably present in the composition. Normally the ratio of contents of long chain saturated primary alcohol and/or "derivative" to conditioning agent(s) will be in the range of 0.2 to 5, preferably in the range of 0.3 to 3, with ratios of 0.5 to 2 and about 1 being more and most preferred, respectively.

In the shampoos the total proportion of detergent, usually anionic detergent or primarily anionic detergent, will normally be in the range of 1 or 2 to 35%, preferably 5 to 30% and often more preferably 5 to 20 or 25%, such as 10 to 20%, e.g., about 15%. Such detergent will preferably be anionic detergent(s) only, and of the weight thereof at least 20%, preferably at least 40%, and in some instances even as high as 70% or up to 100%, may be of the lower molecular weight alkyl group ($C_{6-10}$) type, as previously described, but even as little as 3% is noticeable.

In one type of the invented shampoo, comprising lipophile sulfate (anionic detergent), quaternary ammonium salt, water insoluble hair conditioning agent and water there will usually be present 5 to 35% of such anionic detergent, preferably 5 to 20 or 25%, which may include, in some formulas, 5 to 18% of fatty alcohol sulfate, preferably as its sodium or ammonium salt, 1 to 10% of fatty alcohol ether sulfate, preferably as its sodium or ammonium salt, 0.2 to 2% of quaternary ammonium salt (which sometimes may be omitted), 0.5 to 5% of water insoluble hair conditioning agent, 65 to 85% of water and any balance of shampoo adjuvant(s). Preferred ranges are 10 to 15%, 1 to 5%, 0.3 to 1.0%, 1 to 3.5% and 65 to 80%, respectively. Such compositions may also comprise 0.2 to 2% of hydroxyethyl cellulose, 2 to 5% of lauric monoethanolamide, and/or cocodiethanolamide, 0.5 to 2% of microcrystalline wax and 0.5 to 1 or 2% of petrolatum. When the described aminosilicone is present its concentration will be in the range of 0.5 to 10% and the amount of long chain alcohol or "derivative" will desirably be in the 0.5 to 5% range.

Other preferred formula types comprise the same proportions of anionic detergents (at least 5% and preferably at least 20% thereof being hexyl-, octyl- or decyl-containing), long chain alcohol or "derivative", cationic conditioner, other water insoluble conditioning agent(s), water and shampoo adjuvant(s) as in the preceding formula but also may include as supplementing conditioning agents, 0.3 to 0.5% of $C_{18-36}$(mixed) acid triglyceride, preferably 0.3 to 2%, 0.5 to 3, such as 0.5 to 2%, of microcrystalline wax and 0.5 to 3%, e.g. 0.5 to 1%, of petrolatum, and 0.1 to 3%, such as 0.2 to 2%, of higher ester, such as stearyl stearate. Instead of the microcrystalline wax and petrolatum there may be substituted 0.5 to 1.5% of polyethylene (MW=1,000 to 4,000) and 0.5 to 2% of mineral oil (MW=300 to 800). All such compositions may also include 2 to 5% of lauric monoethanolamide and 0.2 to 2% of hydroxyethyl cellulose.

For gels, pastes, thicker cremes and cake materials within the invention the required, optional and adjuvant components will normally be in the same ranges of proportions as in the aqueous compositions, with the proportion of water often being decreased, sometimes to as low as 30 or 40%. Also, the water may be replaced, up to 50% thereof in some special instances, but usually to no more than 20%, by another solvent, e.g., ethanol or isopropanol.

The proportions of $C_6$, $C_8$ and/or $C_{10}$ alkyl sulfate and $C_6$, $C_8$ and/or $C_{10}$ alkyl lower alkoxy sulfate, water insoluble conditioning agent and aqueous medium are in the ranges of 0.5 to 25%, 0.5 to 10% and 34 to 99%, respectively.

Although the hair conditioning compositions of this invention may be in the various physical forms mentioned, preferably they are in liquid form, such as a stable suspension or lotion. Such compositions should be stable chemically and physically to be acceptable in the marketplace. They should not deteriorate to an unacceptable extent on storage, and should not have components settling out or phases separating during storage. The presence of the mentioned long chain primary alcohols (of the Unilin or Unithox type[s]) improves the stabilities of the invented compositions, in addition to giving them an attractive pearlescent appearance and improving conditioning. Also, such shampoos will be of desirable viscosities, so as to be pourable, and yet will not be so thin that they run uncontrollably. The desired viscosity range is approximately 1,000 to 15,000 centipoises at room temperature (25° C.), preferably 3,000 to 6,000 centipoises. The invented shampoos are non-settling and non-separating, and do not chemically deteriorate on storage, as has been established by accelerated aging tests at elevated temperatures. The stability of the described shampoos is also promoted by incorporation in the shampoo formula of the long chain alcohol or "derivative" component, but can also be improved by the presence of other stabilizers, such as those of the acyl type. The shampoo viscosity may change slightly on storage but that change can be planned for and the formula and manufacturing process can be designed to control viscosity accordingly.

The improved hair conditioning obtained by use of the invented compositions, compared to controls, from which the mentioned conditioning agents and $C_{6-10}$ alkyl-containing anionic detergents have been omitted, is noticeable to users of the shampoos and is measurable in standard tests that are used to evaluate conditioning and its components, including ease of wet combing, ease of dry combing, manageability, static charge retention and flyaway. The shampooer will note that the hair is easier to comb after shampooing, in both wet and dry states, compared to control hair washed with a shampoo that is not under the invention (with $C_{6-10}$ alkyl compound anionic detergent missing from it). Scientific tests also prove that the force needed to move a comb through a standard hair tress after treatment (shampooing) of the hair with an invented shampoo, and rinsing, is measurably less than that when the hair tress is shampooed with a control shampoo. Such results are confirmed by panel tests, in which several experienced evaluators, using both the experimental and control products in blind tests, evaluate them for such combing ease, manageability and static characteristics and effects on the shampooed hair.

Uses of the invented compositions, including the shampoo, are not required to be different from normal uses of hair conditioning shampoos and other hair conditioning compositions. Conditioning compositions may be applied at room temperature or at somewhat elevated temperature in normal quantities and may be left on the hair for different lengths of time, depending on the extent of conditioning desired. Usually the conditioning agent and the hair will be at a temperature in the range of 15° to 50° C., preferably 20° to 40° C., and the conditioning composition will be in contact with the hair for from 30 seconds to ten minutes, preferably for one to five minutes. The amount of shampoo applied will normally be in the range of 0.5 to 50 grams, often 2 to 15 or 20 grams and frequently five or ten grams per use. The shampoo is applied to the hair and is used to wash and condition it, after which it is rinsed off with water after remaining on the hair as an aqueous foam for a sufficient length of time, usually 1 to 5 minutes, so as satisfactorily to condition the hair. The hair is then wet combed, dried, as by blow drying, and dry combed or brushed to the desired style.

To manufacture the present shampoo no complex procedures have to be followed, but to obtain best stability, viscosity and appearance, and greatest conditioning activity, it will be desirable to form a dispersion of the water soluble anionic detergent(s) and adjuvants in water at an elevated temperature, such as 70° to 95°, melt together and/or dissolve lipophilic materials, such as quaternary ammonium salt, hydrocarbons, including polyethylene, mineral oil, microcrystalline wax, petrolatum, paraffin and isoparaffin, long chain alcohol and/or "derivative", $C_{18-36}$ fatty acids and/or triglyceride, and higher fatty ester, e.g., stearyl stearate, to produce a melt or liquid mix at elevated temperature, and admix the two mixes at such elevated temperature, after which heated silicone and/or aminosilicone may be admixed with the resulting mix (it may sometimes also be included with the lipophiles), with the various mixings taking place with the parts to be mixed being at approximately the same temperatures. It is sometimes desirable for the silicone or aminosilicone to be mixed in after the main pre-mixing to promote better stability of the product. When adjuvants are present those which are water soluble and/or dispersible may be mixed in with the aqueous phase materials and those which are not water soluble or dispersible in the aqueous medium may be blended in with the lipophilic materials, such as the hydrocarbons, or in some instances may be added to the mixture of the hydrophilic and lipophilic materials either before or after cooling to room temperature. Normally perfume will be added to the other mixed components after cooling to room temperature but the silicone and/or aminosilicone will usually be added at elevated temperature and before such cooling. The perfume is added to the cooled composition to avoid losses thereof due to volatilizations of components and to prevent any degradation due to heating it. When the procedure described is not followed, as when the various components of the compositions are blended indiscriminately, less stable products can result, which can separate on storage.

The following examples illustrate but do not limit the invention. Unless otherwise indicated all parts are by weight and all temperatures are in degrees Centigrade in the examples, other parts of the specification, and in the claims.

EXAMPLES 1-5

EXAMPLES 1-5

| Component | % (by weight) | | | | |
| --- | --- | --- | --- | --- | --- |
|  | 1 | 2 | 3 | 4 | 5 (control) |
| Hydroxyethyl cellulose (Natrosol ™ 250 HHR, Aqualon Corp.) | 0.45 | 0.45 | 0.45 | 0.45 | 0.45 |
| Hydroxyethyl cellulose (Natrosol ™ 330 CS, Aqualon Corp.) | 0.15 | 0.15 | 0.15 | 0.15 | 0.15 |
| Ammonium lauryl sulfate | — | 6.25 | 9.34 | — | 12.50 |
| Sodium lauryl diethoxy ether sulfate | — | 1.25 | 1.88 | — | 2.50 |
| Sodium decyl triethoxy ether sulfate | 15.00 | 7.50 | 3.75 | — | — |
| Sodium decyl sulfate | — | — | — | 15.00 | — |
| Lauric monoethanolamide | 3.50 | 3.50 | 3.50 | 3.50 | 3.50 |
| Ethylene glycol distearate | 0.75 | 0.75 | 0.75 | 0.75 | 0.75 |
| Stearyl stearate | 0.35 | 0.35 | 0.35 | 0.35 | 0.35 |
| $C_{18-36}$ triglyceride (Syncrowax ™ HGL-C, Croda Corp.) | 0.75 | 0.75 | 0.75 | 0.75 | 0.75 |
| Tricetyl methyl ammonium chloride | 0.50 | 0.50 | 0.50 | 0.50 | 0.50 |
| Distearyl dimethyl ammonium chloride | 0.25 | 0.25 | 0.25 | 0.25 | 0.25 |
| Microcrystalline wax (M.P. = 82° C.) | 1.00 | 1.00 | 1.00 | 1.00 | 1.00 |
| Petrolatum, white (Alba Protopet) | 1.50 | 1.50 | 1.50 | 1.50 | 1.50 |
| Propylene glycol | 0.50 | 0.50 | 0.50 | 0.50 | 0.50 |
| Deionized water | 75.30 | 75.30 | 75.33 | 75.30 | 75.30 |
|  | 100.00 | 100.00 | 100.00 | 100.00 | 100.00 |

Compositions of Examples 1-5 are made by the method described in the specification, with mixings of the hydrophilic components, separate mixings of the lipophilic components and admixings thereof, all being conducted at elevated temperature, e.g., about 80° C., followed by admixings of any non-volatile silicone and/or aminosilicone component(s), when utilized, sodium chloride, to adjust viscosity, and sodium citrate or citric acid, to adjust pH, when such adjusting agents are utilized. Finally, the perfume will be admixed with the cooled unperfumed shampoo at about room temperature (25° C.), at which temperature the shampoo is pearlescent, especially when the long chain alcohol or "derivative" is present in the formula. Base shampoo formulas, without long chain alcohol or "derivative", silicone and/or aminosilicone, pH adjuster, viscosity modifier and perfume, are given herein. In formulas of subsequent examples such and other components of the shampoos will also be present.

The products made are attractive satisfactorily flowing liquid shampoos of viscosities that are less than 6,000 centipoises at 25° C. and their pH's are in the range of 5 to 7. All are sufficiently stable under ordinary storage conditions so as to be marketable, with no objectionable separation or settling out of components. When tested for hair conditioning capabilities, according to the tests described in the specification, they will be found to be good hair conditioning shampoos, with the compositions of Examples 1–4 being better than the control composition of Example 5, in such respect, which is attributed to the presence of the decyl sulfate and/or decyl ethoxy sulfate anionic detergent(s) in the formulas of Examples 1–4, instead of higher alkyl-containing detergents. The compositions of Examples 1 and 4 are better in hair conditioning than those of Examples 2 and 3, which is attributed to the presences of more of the decyl ethoxy sulfate (Example 1) and decyl sulfate (Example 4) than are in the other formulas.

The decyl-containing anionic detergents of the formulas of Examples 1–4 are of the broad range alkyl or conventional types, which are the normal detergents of commerce (for such products). However, when narrow range types are employed, wherein 80% or more of the alkyls, up to 100%, are within the range of 6 or 8 to 12 carbon atoms and 80% or more of the diethoxy and/or triethoxy groups are within the range of 1 ethoxy group to either side of that specified, for example, from 2 to 4 ethoxies for triethoxy, improved hair conditioning is obtainable and the shampoos tend to be thicker, which is a desirable characteristic. Also, it has been found that employment of a perfume identified as CP Paris K3-156 New Revised 3, also helps to increase the shampoo viscosity to a desirable extent.

In other variations of the formulas of these examples other anionic detergents may be substituted for the ammonium lauryl sulfate and sodium lauryl diethoxy sulfate, such as sodium $C_{16}$ olefin sulfonate, sodium coco monoglyceride sulfate, sodium $C_{14}$ paraffin sulfonate and sodium cetyl sulfate. Alternatively, ammonium, triethanolamine and potassium salts may be employed, and the results obtained will be essentially the same as those of the examples wherein ammonium lauryl sulfate and sodium lauryl diethoxy sulfate are present instead. Similarly, the salt-forming cations may be changed for the decyl-containing detergents and the decyl group may be replaced by hexyl and/or octyl, or mixtures of all three.

EXAMPLES 6–9

| Component | % (by weight) | | | |
|---|---|---|---|---|
| | 6 | 7 | 8 | 9 |
| Ammonium decyl sulfate | 12.50 | 12.50 | 12.50 | 12.50 |
| Sodium decyl diethoxy sulfate | 2.50 | 2.50 | 2.50 | 2.50 |
| Distearyl dimethyl ammonium chloride | 0.50 | 0.50 | 0.50 | 0.50 |
| Aminosilicone A (Dow-Corning) | 1.50 | 1.50 | 1.50 | — |
| Long chain ($C_{30\ average}$) alcohol | 2.50 | 2.50 | 1.50 | 2.50 |
| Long chain ($C_{40\ average}$) alcohol | — | — | 1.00 | — |
| Unithox 550 long chain ($C_{40\ average}$) alcohol ethoxylate (13 EtO) | — | — | 1.00 | — |
| Microcrystalline wax (M.P. = 82° C.) | 1.00 | — | — | — |
| Petrolatum, white | 0.75 | — | — | — |
| Syncrowax HGL-C ($C_{18-36}$ triglyceride) | — | — | 1.00 | — |
| Polyethylene 617-A (Allied Corp.) | — | 0.75 | — | 0.75 |
| Paraffin wax (M.P. = 53° C.) | — | 0.35 | — | 0.35 |
| Mineral oil (Britol 50) | — | 1.00 | — | 1.00 |
| Isopar M (isoparaffin) | — | 0.25 | — | 0.25 |
| Lauric monoethanolamide | 3.50 | 3.50 | 3.50 | 3.50 |
| Hydroxyethyl cellulose 250 HHR | 0.57 | 0.67 | — | 0.67 |
| Hydroxyethyl cellulose 330 CS | 0.18 | 0.23 | — | 0.23 |
| Preservative | 0.50 | 0.50 | 0.50 | 0.50 |
| NaCl | 0.20 | 0.20 | 0.20 | 0.20 |
| Sodium citrate | — | — | 0.25 | — |
| Colorant | 0.10 | 0.10 | 0.10 | 0.10 |
| Perfume | 0.80 | 0.80 | 0.80 | 0.80 |
| Deionized Water | 72.90 | 72.15 | 73.15 | 73.65 |
| | 100.00 | 100.00 | 100.00 | 100.00 |

The shampoo compositions of these examples are made by the method described with respect to Examples 1–4 and also in the specification, and it is found that all the shampoos made are attractive in appearance, of desirable viscosities and pH's and are stable at both normal and elevated temperature storage conditions so that separation on storage is avoided. More important, they are excellent hair conditioning shampoos and are better than control shampoos of identical formulas but with the ammonium decyl sulfate and sodium decyl diethoxy sulfate components being replaced by ammonium lauryl sulfate and sodium lauryl diethoxy sulfate, respectively. When the decyl-containing detergents are replaced by corresponding hexyl- and/or octyl-containing detergents the shampoos made also have the desirable properties of the decyl formulas.

The perfume employed is one identified by Colgate-Palmolive Company as their JCH-FLYA-007-C, New No. 3, revised, and such perfume or certain component(s) thereof has a noticeable and desirable effect on increasing the viscosity of the shampoo, whether or not any thickener, like the hydroxyethyl cellulose, is present. Thus, the perfume supplements the thickening action of the decyl-containing anionic detergent, and helps to bring the viscosity into the 3,000 to 6,000 centipoises range, at room temperature (25° C.). Such effects are also obtained when the perfume is included in the other formulas of these examples.

EXAMPLES 10–12

| Component | % (by weight) | | |
|---|---|---|---|
| | 10 | 11 | 12 |
| Ammonium decyl sulfate | 12.50 | 12.50 | 12.50 |
| Sodium decyl ether sulfate (2 EtO per mole) | 2.50 | 2.50 | 2.50 |
| Distearyl dimethyl ammonium chloride | 0.50 | 0.50 | 0.50 |
| Aminosilicone A (Dow-Corning) | 2.50 | — | 1.50 |
| Long chain alcohol (Unilin ™ 425, Petrolite Corp.) | 2.50 | 2.50 | 2.50 |
| Polyethylene (M.W. = 2,000, Allied Corp.) | — | 0.75 | 0.75 |
| Microcrystalline Wax (M.P. = 82° C.) | 1.00 | — | — |

EXAMPLES 10-12-continued

| Component | % (by weight) | | |
|---|---|---|---|
| | 10 | 11 | 12 |
| Paraffin wax (M.P. = 53° C., Boler Petroleum Corp.) | — | 0.35 | 0.35 |
| Isoparaffins (Isopar ™ M, Exxon Corp.) | — | 0.25 | 0.25 |
| Petrolatum, white (Alba Protopet ™) | 0.75 | — | — |
| Mineral oil (Britol ™ 50, Boler Petroleum Corp.) | — | 1.00 | 1.00 |
| Hydroxyethyl cellulose 250 HHR (Aqualon Corp.) | 0.57 | 0.67 | 0.67 |
| Hydroxyethyl cellulose 330 CS (Aqualon Corp.) | 0.18 | 0.23 | 0.23 |
| Lauric monoethanolamide | 3.50 | 3.50 | 3.50 |
| Sodium chloride | 0.20 | 0.20 | 0.20 |
| Preservative (Germaben ™ II) | 0.50 | 0.50 | 0.50 |
| Perfume | 0.80 | 0.80 | 0.80 |
| Colorant | 0.10 | 0.10 | 0.10 |
| Deionized water | 71.90 | 73.65 | 72.15 |
| | 100.00 | 100.00 | 100.00 |

The shampoo compositions of these examples are also made by the procedure described in the preceding examples. Shampoos resulting are of satisfactory appearance, viscosity and pH, and are stable under usual and elevated temperature storage conditions. The shampoos made are better in conditioning effects, including manageability, dry combing and wet combing, compared to "control" formulas in which the ammonium decyl sulfate is replaced by ammonium lauryl sulfate and the sodium decyl ether sulfate (2 EtO per mole) is replaced by sodium lauryl ether sulfate (2 EtO per mole).

EXAMPLES 13-15

EXAMPLES 13-15

| Component | % (by weight) | | |
|---|---|---|---|
| | 13 | 14 | 15 |
| Ammonium decyl sulfate | 12.50 | 12.50 | 12.50 |
| Sodium decyl diethoxy sulfate | 2.50 | 2.50 | 2.50 |
| Distearyl dimethyl ammonium chloride | 0.50 | 0.50 | 0.50 |
| Aminosilicone A (Dow-Corning) | 1.50 | — | 1.50 |
| Long chain linear alcohol (Unilin 425, Petrolite Corp.) | 1.50 | 1.50 | 1.50 |
| Long chain linear alcohol (Unilin 550, Petrolite Corp.) | 1.00 | 1.00 | 1.00 |
| Long chain linear alcohol ethoxylate (Unithox ™ 550, Petrolite Corp.) | 1.00 | 1.00 | 1.00 |
| $C_{18-36}$ triglyceride (Syncrowax HGL-C, Croda Corp.) | 1.00 | 1.00 | 1.00 |
| Paraffin wax (M.P. = 53° C., Boler Petroleum Corp.) | — | 0.35 | 0.35 |
| Polyethylene 617-A (Allied Corp.) | — | 0.75 | 0.75 |
| Mineral oil (Britol 50, Boler Petroleum Corp.) | — | 1.00 | 1.00 |
| Isoparaffin (Isopar M, Exxon Corp.) | — | 0.25 | 0.25 |
| Lauric monoethanolamide | 3.50 | 3.50 | 3.50 |
| Preservative (Germaben II) | 0.50 | 0.50 | 0.50 |
| Sodium citrate | 0.25 | 0.25 | 0.25 |
| Perfume | 0.80 | 0.80 | 0.80 |
| Colorant | 0.10 | 0.10 | 0.10 |
| Deionized Water | 73.35 | 72.50 | 71.00 |
| | 100.00 | 100.00 | 100.00 |

The shampoos of these examples are made in the manner previously indicated and are tested by similar practical and instrumental testing techniques. As a result of such testing it is found that the shampoos made are stable and very effective hair conditioning shampoos which do not separate at elevated temperature storage test conditions, and which condition the hair better than "control" shampoos wherein the ammonium decyl sulfate is replaced by ammonium lauryl sulfate and the sodium decyl diethoxy sulfate is replaced by sodium lauryl diethoxy sulfate.

EXAMPLES 16-18

EXAMPLES 16-18

| Component | % (by weight) | | |
|---|---|---|---|
| | 16 | 17 | 18 |
| Filtered irradiated deionized water | 69.68 | 69.28 | 71.64 |
| Hydroxyethyl cellulose (Natrosol 250 HHR) | — | 0.20 | — |
| Ammonium lauryl sulfate | 7.50 | 7.50 | 11.25 |
| Sodium lauryl diethoxy ether sulfate | 2.50 | 2.50 | — |
| Sodium decyl triethoxy ether sulfate | 5.00 | 5.00 | 3.75 |
| Lauric monoethanolamide | 3.50 | 3.50 | — |
| Monobasic ammonium phosphate (buffer) | — | — | 0.10 |
| Microcrystalline wax (Multiwax ™ 180-M, Witco Chemical Corporation) | 1.00 | 1.00 | — |
| Petrolatum, snow white, Alba Protopet, Witco Chemical Corporation) | 2.00 | 2.00 | — |
| Distearyl dimethyl ammonium chloride | 0.50 | 0.50 | — |
| Unilin 425 ($C_{30}$ (average)) linear alcohol, Petrolite Corp.) | 2.40 | 2.50 | — |
| Unilin 550 ($C_{40}$ (average)) linear alcohol Petrolite Corp.) | 2.40 | 2.50 | — |
| Cocodiethanolamide (Standamid KD) | — | — | 5.00 |
| Aminosilicone A (Dow Corning) | 1.50 | 1.50 | 3.00 |
| Perfume (CP Paris K3-156 new revised 3) | 0.80 | 0.80 | 0.80 |
| Preservative (Germaben II) | 0.50 | 0.50 | 0.50 |
| Dye mix (0.44% aqueous solution) | 0.71 | 0.71 | 0.71 |
| Citric acid, anhydrous | 0.01 | 0.01 | — |
| Sodium chloride | — | — | 0.25 |
| | 100.00 | 100.00 | 100.00 |

Shampoos of the above formulas are made in the manner previously described, with the materials in the first group being mixed together in the aqueous medium, the materials of the second group being melted together and admixed with the aqueous mix, the aminosilicone being admixed with such mixture, and the last group of adjuvants being admixed with the previous admixture after cooling thereof to room temperature. Products resulting are all attractive looking pearlescent lotion shampoos of desirable pH and viscosity in the ranges previously given and they condition hair shampooed with them as well as or better than the leading commercial hair conditioning shampoos. The products are stable on storage, as shown by elevated temperature storage tests.

When pure $C_{30}$ and $C_{36}$ long chain linear alcohols are substituted for the broader range distribution long chain alcohols o the examples similar results are obtainable, with the shampoos of su formulas being pearlescent, lotion-like in appearance, of desirable viscosity and of excellent hair conditioning properties. Similarly, when other non-volatile silicones and dimethicones are employed in replacement of the Aminosilicone A, acceptable products result, although the conditioning is usually not as good as that obtained when similar proportions of Aminosilicone A are employed. Also, when instead of the decyl sulfate and decyl ethoxy sulfate there are substituted the corresponding hexyl and octyl compounds improved conditioning, of essentially the same type as that with the decyl compounds, is obtainable.

EXAMPLE 19

EXAMPLE 19

| Component | % (by weight) |
| --- | --- |
| Deionized water | 72.00 |
| Ammonium lauryl sulfate | 12.50 |
| Sodium hexyl sulfate | 2.50 |
| Monobasic ammonium phosphate | 0.20 |
| Unilin 425 | 3.00 |
| Cocodiethanolamide | 5.00 |
| Aminosilicone A | 3.00 |
| Perfume | 0.80 |
| Preservative | 0.50 |
| Sodium chloride | 0.50 |
| | 100.00 |

EXAMPLES 20-23

EXAMPLES 20-23

| | % (by weight) | | | |
| --- | --- | --- | --- | --- |
| Component | 20 | 21 | 22 | 23 |
| Deionized water | 72.00 | 75.10 | 75.10 | 75.10 |
| Natrosol 250 HHR | — | 0.45 | 0.45 | 0.45 |
| Natrosol 330 CS | — | 0.15 | 0.15 | 0.15 |
| Ammonium lauryl sulfate | 9.00 | 12.12 | 11.87 | 11.25 |
| Sodium octyl diethoxy ether sulfate | 6.00 | 0.45 | 0.75 | 1.50 |
| Sodium lauryl diethoxy ether sulfate | — | 2.43 | 2.38 | 2.25 |
| Monobasic ammonium phosphate | 0.20 | — | — | — |
| Unilin 425 | 3.00 | — | — | — |
| Cocodiethanolamide | 5.00 | — | — | — |
| Lauric monoethanolamide | — | 3.50 | 3.50 | 3.50 |
| Ethylene glycol distearate | — | 0.75 | 0.75 | 0.75 |
| Stearyl stearate | — | 0.35 | 0.35 | 0.35 |
| Syncrowax HGL-C | — | 0.75 | 0.75 | 0.75 |
| Tricetyl methyl ammonium chloride | — | 0.50 | 0.50 | 0.50 |
| Distearyl dimethyl ammonium chloride | — | 0.25 | 0.25 | 0.25 |
| Microcrystalline wax | — | 1.00 | 1.00 | 1.00 |
| Petrolatum | — | 1.50 | 1.50 | 1.50 |
| Aminosilicone A | 3.00 | — | — | — |
| Propylene glycol | — | 0.50 | 0.50 | 0.50 |
| Perfume | 0.80 | — | — | — |
| Germaben II (preservative) | 0.50 | 0.20 | 0.20 | 0.20 |
| Sodium chloride | 0.50 | — | — | — |
| | 100.00 | 100.00 | 100.00 | 100.00 |

The compositions of Examples 20-23 are made in the manner previously described and are all satisfactory conditioning shampoos, with conditioning properties equal to or better than leading commercial conditioning shampoos. In the composition of Example 20 the aminosilicone is the principal hair conditioning agent, with the long chain higher alcohol contributing to such conditioning while at the same time stabilizing the shampoo and making it pearlescent. In Examples 21-23 the aminosilicone and long chain alcohol are omitted and conditioning is effected by a combination of conditioning agents In Examples 20-23 sodium octyl diethoxy ether sulfate is employed in conjunction with ammonium lauryl sulfate as the detergent, and the octyl-containing detergent helps to increase the conditioning action of the conditioning components of the shampoo.

EXAMPLE 24

In the preceding examples, wherein the preferred ammonium decyl sulfate and sodium decyl ethoxy sulfate mixtures are employed in conjunction with the described water insoluble conditioning agent(s) and cationic surfactant, it has been possible to make improved hair conditioning compositions, such as shampoos, which are as good as or better in conditioning properties that other such compositions now being marketed. Similar results are obtainable when other decyl-containing and/or corresponding hexyl- and octyl-containing sulfates and ethoxy sulfates are substituted for the decyl compounds of the examples, as their sodium, ammonium and triethanolamine salts. Also, for examples, the sodium decyl diethoxy sulfate can be replaced by ethoxy sulfates wherein the ethoxy group is of 1 or 3 to 6 carbon atoms, preferably 3, the sodium is replaced by ammonium or triethanolamine, and the decyl is replaced by hexyl or octyl. In like manner the distearyl dimethyl ammonium chloride, if present, may be replaced by other quarternary ammonium salts, such as tricetyl methyl ammonium bromide or chloride, dilauryl dimethyl ammonium chloride, and sometimes even by trimethyl stearyl ammonium chloride or the corresponding tallowyl compounds (in which the alkyl is that obtained form beef tallow). Variations in the mentioned water insoluble hair conditioning agents may be made, utilizing other embodiments of such materials within the description given in the specification, including other long chain primary alcohols and ethoxylated such alcohols of an average of 24 to 45, preferably 30 to 40, carbon atoms int he alcohol chain, and corresponding esters and acids, and the aminosilicone may be changed to be of different substituents and molecular weights within the formula given, and sometimes even non-volatile, dispersible silicones and dimethicones (which do not contain any amino groups) may be employed, such as those disclosed and illustrated in U.S. Pat. No. 4,704,272. Various of the mentioned water insoluble conditioning agents may be substituted and/or added, and various adjuvants may be substituted for and/or added to those in the given formulas. For example, the lauric monoethanolamide or cocodiethanolamide may be replaced by lauric myristic mono- or diethanolamides or isopropanolamides or by corresponding lauryl and coco amides. EDTA may be included, and the hdyroxylated ethyl celluloses may be replaced by hydroxypropylmethyl celluloses, methyl cellulose or natural gums, e.g., gaur gum.

The aminosilicones may be replaced by non-amino silicones and diemthicones too, such as the compounds of U.S. Pat. No. 4,704,272, and the cationic conditions may be replaced by the suitable disclosed substitutes or equivalents. The compositions made of various such different formulas will also be high quality, satisfactorily conditioning, stable and attractively pearlescent shampoos of desired pH and viscosity.

The proportions of the various components of the described compositions of this example and of Examples 1-4 and 6-23 may be varied ±10%, ±20% and ±30%, while still remaining within the ranges mentioned in the specification, and hair conditioning shampoos of improved hair conditioning properties will result. Also, when the "conventional" longer chain alkyl-containing anionic detergent(s) of the shampoos described herein, especially of the working examples, are modified so as to include hexyl-, octyl- and/or decyl-containing detergents in replacement of some of the higher alkyl-containing anionic detergents, better hair conditioning effects are obtained.

When the present shampoos or the variations of the invention that have been described are used as conditioning hair shampoos, according to methods described herein, which include application thereof to the hair, in the presence of additional water, followed by rinsing, the hair is satisfactorily cleaned and conditioned. It may be combed more readily when wet or dry, does not control shampoos and will be more manageable and softer to the touch than hair shampooed with such controls.

The present invention is in large part an improvement over the invention described in a patent application of Patel and Robbins, entitled Hair Conditioning Shampoo Containing Long Chain Alcohol Component, which is being filed on the same day as the present application. Therefore, the various shampoos described therein can also be improved further in hair conditioning properties by replacing a part of any $C_{12}$ and higher lipophile-containing detergent with the corresponding or other hexyl-, octyl- and/or decyl-containing detergent compounds.

The various patents, patent applications and publications previously referred to in this specification are hereby incorporated herein by reference.

This application is a continuation-in-part of previous patent applications Ser. Nos. : 07/369,361; 07/369,389; 07/432,644; and 07/432,952. Ser. Nos. 07/432,644 and 07/432,952 are each continuations-in-part of Ser. No. 07/369,361.

The invention has been described, with reference to illustrations and examples thereof but is not intended to be limited to these because it is evident that one of skill in the art, with the present specification before him or her, will be able to utilize substitutes and equivalents without departing from the invention.

What is claimed is:

1. A hair conditioning shampoo of improved hair conditioning properties due to the content of $C_{6-10}$ alkyl sulfates $C_{6-10}$ alkyl $C_{1-6}$ alkoxy or polyalkoxy sulfates, and mixtures thereof, wherein the lower alkoxy is of 1 to 6 carbon atoms, which comprises 0.5 to 25% of an anionic detergent selected from the group consisting of $C_{6-10}$ alkyl sulfates, $C_{6-10}$ alkyl $C_{1-6}$ alkoxy and polyalkoxy sulfates and mixtures thereof, 0.5 to 10% of water insoluble hair conditioning agent and 34 to 99% by weight of aqueous medium.

2. A hair conditioning shampoos according to claim 1, which is in liquid emulsion or dispersion form and is pearlescent and of improved stability due to its content of 0.5 to 10% of a long chain alkyl-containing compound which is a alcohol, an ethoxylated alcohol, an acid or an ester, containing a hydrocarbon chain of an average of 24 to 45 carbon atoms, or of any mixture of such compounds.

3. A hair conditioning shampoo according to claim 1 which comprises 0.2 to 30% of a cationic conditioning agent which is a quaternary ammonium salt or an amine salt and 0.5 to 5% of a long chain alkyl-containing compound which is a long chain alcohol or a long chain ethoxylated alcohol or a mixture thereof, in which the long alkyl chain is of an average of 24 to 45 carbon atoms, and in which at least one other water insoluble conditioning agent is present, which is selected from the group consisting of silicones, polyethylenes, paraffins, isoparaffins, petrolatums, microcrystalline waxes, $C_{18-36}$ (mixed) fatty acids and/or triglycerides, stearyl stearate, beeswax and mixtures thereof, and the percentage of water in the composition is in the range of 60 to 90%.

4. A shampoo according to claim 3 wherein the cationic conditioning agent is a quaternary ammonium salt of the formula

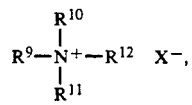

wherein $R^9$ is lower alkyl of 1 to 4 carbon atoms, and $R^{10}$ and $R^{11}$ are higher alkyls of 10 to 40 carbon atoms, $R^{12}$ is such a lower alkyl or such a higher alkyl and $X^-$ is a salt forming ion, the water insoluble conditioning agent includes an aminosilicone of the formula

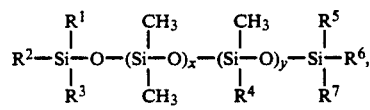

wherein $R^1$, $R^2$, $R^3$, $R^5$ and $R^7$ are alkyls of 1 to 6 carbon atoms, $R^4$ is $-R^8-NH-CH_2CH_2-NH_2$, $R^8$ is alkylene of 3 to 6 carbon atoms, x is an average number in the range of 100 to 10,000 and y is an average number in the range of 0 to 10, which is of an amine equivalent in the range of 4,000 to 60,000, and a long chain alkyl-containing compound is present, which is a long chain alcohol or a long chain ethoxylated alcohol of an average of about 30 to 40 carbon atoms in the long chain alkyls thereof, in which such alkyls are of even numbers of carbon atoms, and which alcohols are of substantially bell-shaped distribution curves (% by weight vs. chain length).

5. A shampoo according to claim 3 wherein the alkyl lower alkoxy sulfate is an alkyl polyethoxy sulfate of 1 to 6 ethoxy groups, the cationic conditioner is a quaternary ammonium salt in which X is chlorine and $R^{10}$ and $R^{11}$ are alkyls of 12 to 20 carbon atoms, a $C_{24-45}$ long chain alcohol and/or an alkoxylated $C_{24-45}$ long chain alcohol is present, the proportions of the total of the $C_{10}$ alkyl sulfate and $C_{10}$ alkyl polyethoxy sulfate, the cationic conditioner, the water insoluble non-cationic conditioning agent, the $C_{24-45}$ long chain alcohol and/or the alkoxylated $C_{24-45}$ long chain alcohol and water are in the ranges of 5 to 25%, 0.1 to 5%, 0.5 to 5%, 0.5 to 10% and 65 to 85%, respectively, which shampoo comprises 0 to 20% of anionic detergent that is of an alkyl chain of more than 10 carbon atoms.

6. A shampoo according to claim 5 which comprises 0.5 to 5% of a long chain alkyl-containing alcohol and/or alkoxylated such alcohol, which is/are of an average of 30 to 40 carbon atoms in the alkyl groups thereof.

7. A shampoo according to claim 5 which comprises 5 to 25% of anionic detergent, of which at least ¼, on a total composition basis, is $C_6$, $C_8$ and/or $C_{10}$ alkyl sulfate, $C_6$, $C_8$ and/or $C_{10}$ alkyl ethoxy sulfate of 2 to 6 ethoxy groups per mole or a mixture thereof, 0.3 to 2% of quaternary ammonium halide, which is a mixture of distearyl dimethyl ammonium chloride and tricetyl methyl ammonium chloride, in a ratio in the range of 0.3 to 3, 0.5 to 3% of microcrystalline wax, 0.5 to 3% of petrolatum, 0.2 to 2% of stearyl stearate, 0.3 to 5% of $C_{18-36}$(mixed) acid triglyceride, and 65 to 80% of water.

8. A shampoo according to claim 7 which comprises 0.2 to 2% of hydroxyethyl cellulose and 2 to 5% of lauric monoethanolamide or cocodiethanolamide.

9. A process for shampooing and conditioning hair which comprises applying to human hair, on the head, a shampooing and conditioning proportion of a shampoo according to claim 1, which contains a conditioning agent, and rinsing the shampoo from the hair, thereby leaving on the hair a such conditioning amount of conditioning agent.

* * * * *